(12) United States Patent
Paul, Jr.

(10) Patent No.: US 6,416,499 B2
(45) Date of Patent: *Jul. 9, 2002

(54) MEDICAL FLUID FLOW CONTROL VALVE

(75) Inventor: Ram H. Paul, Jr., Bloomington, IN (US)

(73) Assignee: Cook Incorporated, Bloomington, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/126,335

(22) Filed: Jul. 30, 1998

Related U.S. Application Data (60) Provisional application No. 60/054,203, filed on Jul. 30, 1997.

(51) Int. Cl.$^7$ .................................................. A61M 5/14

(52) U.S. Cl. .................................. 604/256; 604/167.04

(58) Field of Search .......................... 604/30, 33, 246, 604/249, 256, 283, 905, 533; 137/843, 844, 852, 859, 164.01, 167.01, 167.02, 167.03, 167.04, 167.06, 171

(56) References Cited

U.S. PATENT DOCUMENTS

| | | | |
|---|---|---|---|
| 1,180,665 A | | 4/1916 | McElroy |
| 3,853,127 A | | 12/1974 | Spademan |
| 3,977,400 A | * | 8/1976 | Mooerhead |
| 4,000,739 A | | 1/1977 | Stevens |
| 4,143,853 A | | 3/1979 | Abramson |
| 4,610,665 A | | 9/1986 | Matsumoto et al. |
| 4,626,245 A | | 12/1986 | Weinstein |
| 4,809,679 A | | 3/1989 | Shimonaka et al. |

(List continued on next page.)

FOREIGN PATENT DOCUMENTS

| | | | |
|---|---|---|---|
| EP | 0369314 | * | 11/1989 |
| EP | 0369314 | | 5/1990 |
| EP | 0658357 | | 6/1995 |
| EP | 0771574 | | 5/1997 |

OTHER PUBLICATIONS

US 5,520,663, 05/1996, Patterson et al. (withdrawn)

*Primary Examiner*—Angela D. Sykes
*Assistant Examiner*—LoAn H. Thanh
(74) *Attorney, Agent, or Firm*—Richard J. Godlewski (57) ABSTRACT

A valve (10) useful as a fluid flow check valve or as a self-sealing, penetrable, hemostatic valve for sealing a catheter introducer (12) includes a seal (26) which is highly resistant to tearing and leakage, yet is capable of accepting repeated penetrations by devices of a wide variety of diameters. The seal (26) is disk-shaped and is composed of a thermoplastic styrenic elastomer, such as a styrene-ethylene/butylene-styrene block copolymer, of very low durometer (a hardness of no more than about 30 Shore A). The seal (26) is preferably contained in a valve body (40) and is disposed between a valve seat (48) in the valve body (40) and a cap (56) connected to the valve body (40) and becomes deflected upon assembly of the valve. The seal (26) includes at least one perforation (34) closed by such deflection. This deflection also provides the seal (26) with a proximal or upstream concave surface (30), and this deflection along with the clamping of the periphery of the seal by and between the cap and the valve seat, makes it highly resistant to inversion during repeated removals and manipulations of interventional devices passing through the valve (10). The valve (10) of the present invention is particularly advantageous in that it seals the introducer (12) with a high degree of effectiveness when no interventional device lies across its seal (26), and in that it offers a high resistance to tearing when penetrated by devices of large diameter.

37 Claims, 6 Drawing Sheets

U.S. PATENT DOCUMENTS

| | | | |
|---|---|---|---|
| 4,946,133 A | 8/1990 | Johnson et al. | |
| 4,978,341 A | 12/1990 | Niederhauser | |
| 5,006,113 A | 4/1991 | Fischer | |
| 5,025,829 A | 6/1991 | Edwards et al. | |
| 5,059,186 A * | 10/1991 | Yamamoto | 604/280 |
| 5,071,411 A | 12/1991 | Hillstead | |
| 5,080,654 A | 1/1992 | Picha et al. | |
| 5,098,393 A | 3/1992 | Amplatz et al | |
| 5,125,903 A | 6/1992 | McLaughlin et al. | |
| 5,141,498 A * | 8/1992 | Christian | 604/167 |
| 5,167,637 A | 12/1992 | Okada et al. | |
| 5,211,633 A | 5/1993 | Stouder, Jr. | |
| 5,250,033 A | 10/1993 | Evans et al. | |
| 5,267,966 A | 12/1993 | Paul | |
| 5,273,546 A * | 12/1993 | McLaughlin et al. | 604/167 |
| 5,300,033 A | 4/1994 | Miller | |
| 5,304,156 A | 4/1994 | Sylvanowicz et al. | |
| 5,342,315 A | 8/1994 | Rowe et al. | |
| 5,354,275 A * | 10/1994 | Behnke et al. | |
| 5,409,463 A | 4/1995 | Thomas et al. | |
| 5,409,464 A | 4/1995 | Villalobos | |
| 5,520,655 A | 5/1996 | Davila et al. | |
| 5,545,142 A | 8/1996 | Stephens et al. | |
| 5,639,810 A * | 6/1997 | Smith, III et al. | 524/269 |
| 5,674,206 A * | 10/1997 | Allton et al. | 604/249 |
| 5,707,173 A * | 1/1998 | Cottone et al. | 405/128 |
| 5,824,400 A * | 10/1998 | Petrakis et al. | 428/218 |
| 5,961,497 A * | 10/1999 | Larkin | 604/246 |

* cited by examiner

MEDICAL FLUID FLOW CONTROL VALVE

CROSS REFERENCE TO RELATED APPLICATIONS

This application claims priority of provisional application Ser. No. 60/054,203, filed Jul. 30, 1997.

TECHNICAL FIELD

This invention relates generally to surgical devices, and more particularly to medical devices for controlling the flow of fluids through catheter introducers and other sheaths, cannulae, catheters, trocars, scopes and the like.

BACKGROUND OF THE INVENTION

It is now well known to perform a variety of surgical procedures by the introduction of an interventional device into the body, for example, into an arterial or venous blood vessel, or into a laparoscopic or other cavity artificially maintained in the body. Typical of the former type of procedure are coronary angiography (e.g., where an X-ray contrast fluid is inserted into the coronary artery) and percutaneous transluminal coronary angioplasty (PTCA). These and other procedures involve the introduction of an interventional device, such as a catheter (open or closed end), a wire guide, a balloon, a stent, an atherectomy device, or the like into the vessel or cavity in question. The single generic term "catheter" should be understood herein to include all of such interventional devices, unless the context limits the meaning of the term.

Procedures for introducing a catheter into a blood vessel include the cut-down method and the Seldinger technique. The Seldinger technique is well known, and first involves opening a blood vessel with a needle, inserting a guide wire into the vessel through the lumen of the needle, withdrawing the needle and inserting a dilator over the guide wire. The dilator is located inside an associated sheath which is also inserted into the vessel, and the dilator is sealed to the sheath by a hemostasis or hemostatic valve through which the dilator passes. The dilator is removed, and the catheter inserted through the sheath and hemostatic valve into the vessel.

During the performance of the Seldinger technique and other procedures, care must be taken to avoid the undesirable introduction of air into the vessel (air embolism) and the undesirable leakage of blood, other fluids or a cavity-pressurizing gas from the patient (as much for the protection of health care practitioners as of the patient). As procedures for introducing catheters and other interventional devices have become more widely accepted, the procedures have also become more diverse, and the variety of sizes and types of devices employed has grown dramatically. The risks of inward or outward leakage thus become greater.

Because of such variety in the sizes and types of catheters and other devices to be handled, it would be highly desirable to have a hemostatic seal or other check valve which seals an introducer sheath or other device with a high degree of effectiveness when no catheter or other interventional device lies across the seal or valve, and which is also capable of providing an acceptable seal to catheters and other interventional devices having a wide range of diameters. High resistance to tearing when penetrated by catheters and other interventional devices of large diameter is very desirable as well. It would also be valuable to have a hemostatic seal or other check valve which allowed the easy passage through the seal or valve of devices of a very wide range of diameters, without interfering with tactile feedback from the catheter or other interventional device. Such tactile feedback is also known simply as "feel." It would also be desirable to have a hemostatic seal or other check valve which tolerated repeated insertions and withdrawals of catheters or other interventional devices without any appreciable decrease in the performance characteristics of the seal or valve, especially with respect to leakage and "feel."

A variety of prior devices are known to act as hemostatic or check valves. For example, U.S. Pat. No. 5,273,546 (McLaughlin et al., Dec. 28, 1993) discloses a hemostasis valve including an elastomeric gasket, the gasket having at least one concave surface and a pin hole or slits through the central region of the gasket. The gasket is preferably composed of polyisoprene, but could also be composed of silicone rubber, natural rubber or a thermoplastic elastomer, such as an injection moldable synthetic rubber compound. The gasket material has a hardness of 30–50 Shore A, preferably 35–45 Shore A. One drawback of silicone rubbers and other materials of similar hardness is that such materials offer an inadequately soft and compliant texture, so that the "feel" of the catheter or other interventional device is less than adequate when the catheter or device is rotated or advanced. Selecting a silicone rubber of lower hardness is inadequate because the very low durometer silicone materials (below a hardness of 30 Shore A) do not currently offer the degree of resistance to tearing which would make the valve acceptably durable for surgical use.

U.S. Pat. No. 5,141,498 (Christian, Aug. 25, 1992) is directed to a flexible valve which includes a body having a cylindrical wall with a central bore therein, and at least three flexible leaflets adjoining the central wall. The valve body is composed of an elastomeric material, for example, a urethane compound having a hardness of 20–50 Shore A, preferably 35 Shore A. The patent notes that a "rubber-like" compound identified as "Krayton" can also be used. The valve of the reference is intended to remedy the specific drawbacks associated with the so-called "duckbill" type of valve having only two of such leaflets. Duckbill valves are well known to be subject to several drawbacks, not all of which are mentioned in the patent. First, duckbill valves sometimes invert when relatively large diameter catheters or other interventional devices are inserted through them and then withdrawn. Moreover, they sometimes possess a large well behind them which can trap air or blood therein; this well cannot be flushed out in the conventional manner, that is, by injection through the side arm (or extension tube) commonly present in devices incorporating hemostatic valves. Finally, duckbill valves commonly are unable to maintain a seal under a negative pressure or vacuum. This is seen, for example, when a health care practitioner draws on a syringe connected to the side arm; air is undesirably drawn through the valve and into the syringe and the body containing the valve. The Christian patent thus uses compounds of a specific type (along with the additional leaflet) to cure problems associated with a specific valve construction, and makes no general teachings about such compounds which would apply to other types of valves. Moreover, the patent does not appear to disclose or suggest that all of the indicated compounds were in fact useful over the entire range of hardness specified.

U.S. Pat. No. 5,025,829 (Edwards et al., Jun. 25, 1991) is directed to a parenteral check valve including a preloaded, perforate disk made of a thermoplastic elastomer, an elastomeric material or a thermoplastic material having a hardness of 35 to 100 Shore A. An example of such a material is a "KRATON" brand thermoplastic elastomer.

("KRATON" is believed to be a registered trademark of Shell Chemical Company.) The disk seals against a circular flange or ring on a perforate seat in the valve; fluid pressure moves the disk away from the flange to allow fluid flow through the perforation in the disk.

Finally, U.S. Pat. No. 5,342,315 (Rowe et al., Aug. 30, 1994, incorporating by reference the application leading to U.S. Pat. No. 5,545,142, Stephens et al., Aug. 13, 1996) discloses a variety of trocar seals made from elastomeric materials such as silicone, latex, rubber, polyurethane, "Kraton" (specifically, a thermoplastic elastomer of A-B-A type, in particular, styrene-isoprene-styrene block copolymer) or the like. It is believed that S-I-S type block copolymers typically have a hardness of 30 to 40 Shore A, comparable to the other identified elastomers, all of which lack the durability and resistance to splitting desirable for hemostatic valves and other check valves.

Again, it would be highly desirable to have a hemostatic valve or other check valve which overcomes the various drawbacks associated with these and other devices, as noted above.

SUMMARY OF THE INVENTION

According to the present invention, there is a valve arrangement for controlling the flow of fluid through a medical device, wherein the arrangement comprises a seal to be disposed in the fluid flow, at least one perforation to be found of the seal at least in the region of the or each perforation to close the perforation(s). The material can be compressible, and the means can be designed to deflect the material of the seal, at least in the region of the or each perforation, in order to close the perforation(s) whenever the seal is unpenetrated by the medical device. The seal can be mounted in order to be changed between one state and another state, so that when the seal is in the one or undeflected state, the perforation(s) is open to permit fluid flow, and when in the other or deflected state, the perforation(s) is closed to prevent fluid flow, and in which the means serves to transfer the seal between the states. The material can be of low durometer thermoplastic. Alternatively, in another aspect of the invention, the material of the seal can be of resilient material whereby the seal can be moved between a concave state and a convex state, and wherein the or each perforation is formed in such a manner that the perforation (s) is open in one of the states and closed in the other of the states.

Each perforation(s) can be rectangular in shape and can be lined with a softer material in order to ensure total closure of the perforation(s), even when instruments are passed therethrough.

In yet another aspect of the invention, the foregoing problems are solved and a technical advance is achieved in an illustrative fluid flow check valve, or valve for sealing catheter introducers and the like. The valve of the present invention includes a perforated disk seal which is deflected so as to possess a concave face in the proximal or upstream direction. The disk seal is composed of a low durometer thermoplastic material, preferably a styrene-ethylene/butylene-styrene block copolymer, having a hardness of no more than about 30 Shore A. Unexpectedly, the seal of the present invention is highly resistant to tearing or splitting when repeatedly penetrated by catheters or other interventional devices which would render silicone or other rubber seals of similar hardness useless. Not only is the seal of the present invention resistant to such splitting, the seal also maintains a very good fluid seal against the periphery of the catheter or other inserted device. The present invention is particularly advantageous over the prior art in that it achieves these functions while simultaneously permitting the health care practitioner very good "feel" of the catheter or other device introduced through the seal.

In one aspect, then, the present invention is directed to a valve for a fluid flow path of a medical device, comprising: a seal disposed in the fluid flow path, the seal being composed of a very low durometer thermoplastic styrenic elastomer having a hardness of no more than about 30 Shore A, and the seal having an unstressed condition in which the seal is shaped generally as a disk and has opposed first and second faces and at least one perforation extending through the seal from the first face to the second face; and means connected to the fluid flow path for deflecting the seal so as to close the at least one perforation in the seal.

The first and second faces of the seal define a distal or downstream preferred direction of movement through the at least one perforation through the seal. Such movement is by a catheter or other interventional device when the valve of the present invention is incorporated into an introducer sheath or the like, or by fluid when the valve is a fluid flow check valve.

Preferably, the seal is composed of a thermoplastic styrene-ethylene/butylene-styrene (SEBS) block copolymer having a hardness between about 2 Shore A and 30 Shore A, and more preferably, a hardness of about 13 Shore A to 15 Shore A. Such thermoplastic elastomeric block copolymers have been found to withstand repeated penetrations by catheters and other interventional devices of a wide variety of sizes without tearing or leaking. Materials incorporating "KRATON" G polymers have been found particularly useful for this purpose. (As noted above, "KRATON" is believed to be a trademark of Shell Chemical Company for polymers.)

Also preferably, the deflecting means imparts a concave shape to the first face of the seal, that is, the face that faces outwardly from the valve and which is first penetrated by the catheter or other interventional device. Such a shape has been found to be very important in preventing inversion of the seal during or after rotation or distal movement of the catheter or other device, thereby avoiding undesired leakage from the introducer sheath. A convenient deflecting means for shaping the seal in this manner comprises a valve body defining at least part of the flow path, a valve seat formed in the valve body and a cap engageable with the valve body adjacent to the valve seat. The seal is received between and its periphery is compressed and clamped between the cap and the valve body, preferably, between the cap and the valve seats as well as deflected distally.

The concave shape of the seal can be maintained or augmented by a facing pair of annular flanges located one each on the cap and valve seat, each of the flanges abutting a face of the seal. The cap flange can be formed integrally, that is, as a unit with the remainder of the cap. It is convenient, however, to form the flange on a separate ring received in the cap. The ring is positioned in the opening in the cap through which the catheter or other interventional device is inserted into the flow path.

It is highly preferred that the valve seat is formed as a series of steps in the valve body, the steps decreasing in radius in the distal or downstream direction.

It is also highly preferred that, when the seal is in its unstressed condition, the at least one perforation through the seal is wider at the second face of the seal (the distal or downstream face) than it is at the first face (the proximal or upstream face). The at least one perforation can be Y-shaped in cross-section but can possess a substantial length transverse to that cross-section. Such a perforation is referred to as "Y-shaped." The at least one perforation can alternatively be circular or oval in shape.

In another aspect, the present invention is directed to a device of the type disclosed above, comprising a number of the distinct elements described above. In particular, in this aspect the present invention is directed to a valve for a fluid flow path, comprising: a seal disposed in the fluid flow path, the seal being composed of a very low durometer thermoplastic elastomeric styrene-ethylene/butylene-styrene block copolymer having a hardness of no more than about 30 Shore A, and the seal having an unstressed condition in which the seal is shaped generally as a disk and has opposed first and second faces and at least one perforation extending through the seal from the first face to the second face; and means connected to the fluid flow path for deflecting the seal so as to close the at least one perforation in the seal; wherein the deflecting means comprises a valve body defining at least part of the flow path, a valve seat formed in the valve body and a cap engageable with the valve body, the periphery of the seal being compressed and clamped between the cap and the valve seat; and wherein the cap and the valve seat each include respective annular cap and valve seat flanges facing each other and abutting the first and second faces of the seal, respectively, imparting a concave shape to the first face of the seal; wherein the first and second faces of the seal define a preferred direction of movement through the at least one perforation, and wherein the deflecting means imparts a concave shape to the first face of the seal facing opposite the preferred direction of movement through the at least one perforation; and wherein when the seal is in its unstressed condition, the at least one perforation is wider at the second face of the seal than at the first face of the seal.

In yet another aspect, the present invention is directed to an improvement in a valve for a fluid flow path, the valve including a perforate elastomeric disk closing the flow path, the improvement wherein the disk is composed of a thermoplastic styrene-ethylene/butylene-styrene block copolymer having a hardness of no more than about 30 Shore A.

In still another aspect, the present invention is directed to an improvement in a self-sealing, penetrable, hemostatic valve for an introducer for a catheter or other interventional device, the catheter or other interventional device having a proximal end, and the valve including a generally disk-shaped seal receiving and sealing around the periphery of the catheter or other interventional device when inserted in the introducer, the improvement wherein the seal is composed of a thermoplastic styrene-ethylene/butylene-styrene block copolymer having a hardness of no more than about 30 Shore A, and wherein the seal is deflected so as to present a concave face towards the proximal end of the catheter or other interventional device.

The valve of the present invention is particularly advantageous over prior seals in that it possesses a high degree of effectiveness when no catheter or other interventional device lies across the seal or valve, and simultaneously provides an acceptable seal to catheters and other interventional devices having a wide range of diameters. The valve of the present invention also possesses a high resistance to tearing when penetrated by catheters or other interventional devices of large diameter. The valve of the present invention allows the easy passage devices of a very wide range of diameters without interfering with tactile feedback from them. The valve of the present invention seals well against vacuum or a negative pressure. The valve of the present invention tolerates repeated insertions and withdrawals of catheters or other interventional devices without any appreciable decrease in the performance characteristics of the seal or valve, especially with respect to leakage and "feel." Finally, the valve of the present invention is advantageous in that the distal or inward deflection of the seal along with compression placed upon the seal by clamping of its periphery prevents undue inversion of the seal surface despite repeated removals and manipulations of devices lying across the valve.

BRIEF DESCRIPTION OF THE DRAWINGS

A better understanding of the present invention will now be had upon reference to the following detailed description, when read in conjunction with the accompanying drawing, wherein like reference characters refer to like parts throughout the several views, and in which.

DETAILED DESCRIPTION

Figure 1:
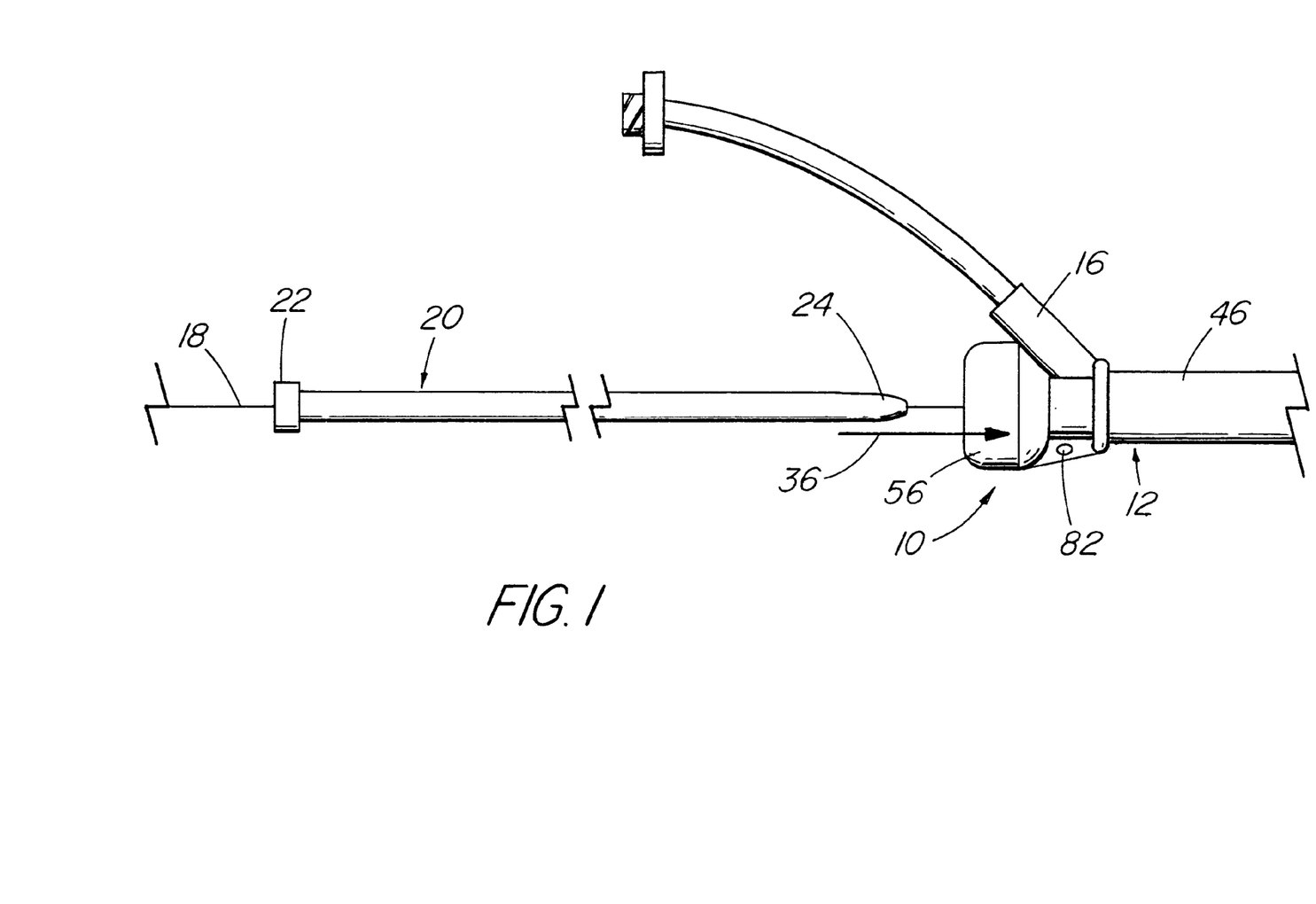
FIG. 1 is a side view of the preferred embodiment of the present invention.

With reference first to FIG. 1 illustrating a preferred embodiment of the present invention, a valve 10 useful as a check valve in a fluid flow path of a medical device, or as a hemostatic valve for an introducer for a catheter or other interventional device, is thereshown. More particularly, the valve 10 is shown as incorporated into a catheter introducer 12, and as such finds particular utility as a self-sealing, penetrable, hemostatic valve. The valve 10 is employed in the conventional fashion. For example, a guide wire is first advanced through the valve 10, in a distal or downstream direction indicated by arrow 36, and into and through a conventional sheath 46 incorporated in the introducer 12. When the guide wire 18 is suitably positioned, an interventional device (exemplified by a catheter 20) is distally advanced over the guide wire 18 by fitting the distal end 24 of the catheter 20 over the proximal end of the guide wire 18. The catheter 20 conveniently includes a proximal end 22 adapted for connection to other medical treatment devices as appropriate. A side arm 16 is provided for its usual functions, as is a suture hole 82 for securing the introducer 12 to a patient or to patient bedding.

Figure 2:
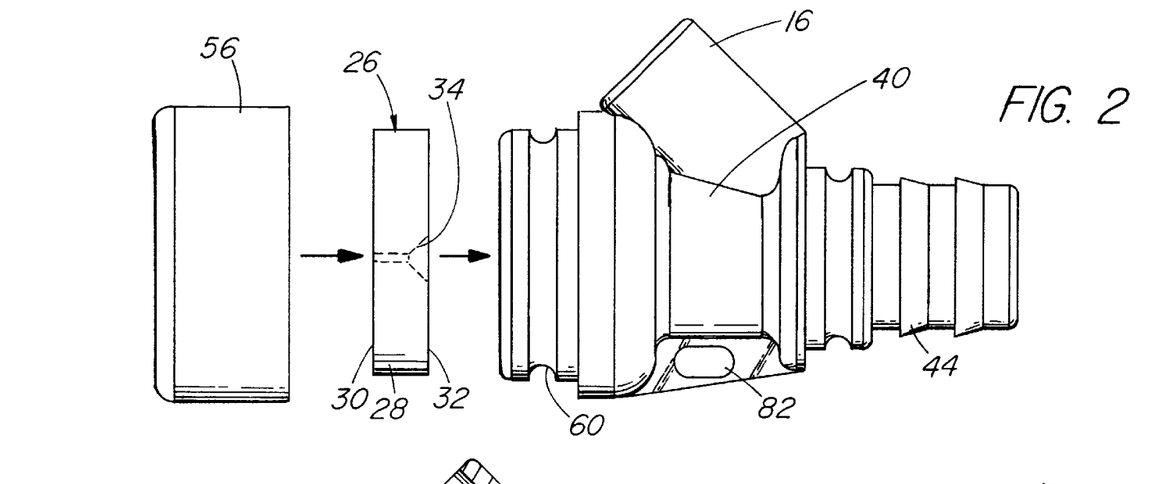
FIG. 2 is an exploded view of a portion of the preferred embodiment of the present invention.
Figure 3:
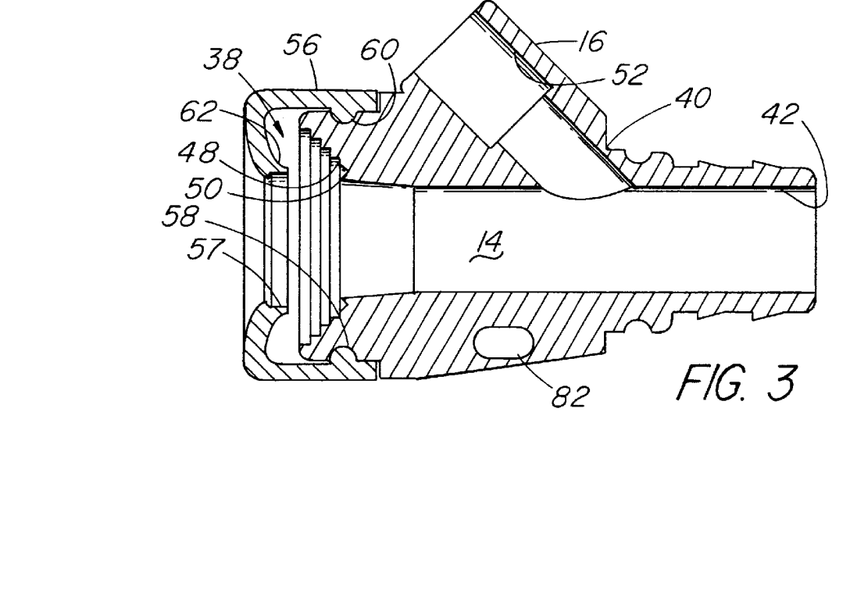
FIG. 3 is a cross-sectional view taken in the plane of FIG. 2, with the cap fitted to the body, and with the seal omitted for clarity.

With reference now to FIGS. 2 and 3, the valve 10 of the present invention first comprises a seal 26 disposed in a fluid flow path 14. The seal 26 is preferably composed of a low durometer thermoplastic styrenic elastomer having a hardness of no more than about 30 Shore A. Other materials exhibiting equivalent properties are contemplated. Preferably, the styrenic elastomer is selected to possess a resistance to tearing equivalent to that possessed by a thermoplastic styrene-ethylene/butylene-styrene block copolymer elastomer having a hardness of no more than about 30 Shore A. Also preferably, the hardness of the elastomer ranges between about 30 Shore A and 2 Shore A. More preferably, the hardness of the elastomer is about 13 Shore A to about 15 Shore A. Most preferably, the elastomer is a styrene-ethylene/butylene-styrene block copolymer. "KRATON" G, and materials containing it, for example, "DYNAFLEX" G, are especially preferred as elastomers for the seal 26 of the present invention. ("DYNAFLEX" is believed to be a trademark of GLS Corporation, Cary, Ill.)

The seal 26 is conveniently formed by thermoplastic molding, and the details of processes of thermoplastic molding should be well known to those skilled in this area; accordingly, no detailed description of the manufacture of the seal 26 need be given here. The seal 26 possesses an initial, unstressed condition in which the seal 26 is generally shaped as a disk 28 having opposed first 30 and second 32 faces, although, other geometric configurations, other than a disk, are clearly contemplated so as to conform with any medical device fluid flow path configurations. The seal 26 also possesses at least one (and, when the valve 10 is employed as a hemostatic valve, preferably only one) perforation 34 extending through it from the first face 30 to the second face 32. As shown in FIGS. 5A–C 6A–C and 9A–B, the seal is so molded to have a perforation 34 that is open in its unstressed condition, with the sidewalls of the perforation being spaced apart along the axial length of the perforation. As seen in FIGS. 5B, 6B and 9B, the first face 30 is shown as planar, and in FIG. 12, the first face is shown as convex, so that upon molding of the seal the first face can be termed nonconcave.

The valve 10 of the present invention also comprises a means 38 connected to the fluid flow path 14 for deflecting the seal 26 so as to close the at least one perforation 34. The deflecting means 38 first comprises a valve body 40 defining at least part of the flow path 14 therein, for example, by a fluid bore 42 formed in the valve body 40. The valve body 40 is composed of a suitable medical grade synthetic or other material. The deflecting means 38 also comprises a cap 56 engageable with the valve body 40, composed of the same or a different medical grade synthetic or other material. The seal 26 is positioned between the cap 56 and the valve body 40 so that, when the cap 56 is engaged with the valve body 40, the periphery of the seal 26 is compressed between the cap 56 and the valve body 40, and is deflected distally or inwardly into the valve. The cap 56 is retained on the valve body 40 by the mating engagement of an inwardly depending annular bead 58 on the interior of the cap 56 with an annular groove 60 on the outside of the valve body 40. The deflecting means 38 also preferably comprises a valve seat 48 formed in the valve body 40. The seal 26 is abutted against the valve seat 48 when the cap 56 is engaged with the valve body 40.

In another aspect of the present invention, the valve 10 can be characterized as a valve arrangement for controlling the flow of fluid through a medical device, wherein the arrangement comprises a seal 26 to be disposed in the fluid flow. At least one perforation is found in the seal to permit fluid flow through the seal. The arrangement also includes means 38, 58 for causing the material of the seal at least in the region of the or each perforation to, close the perforation (s).

Figure 7:
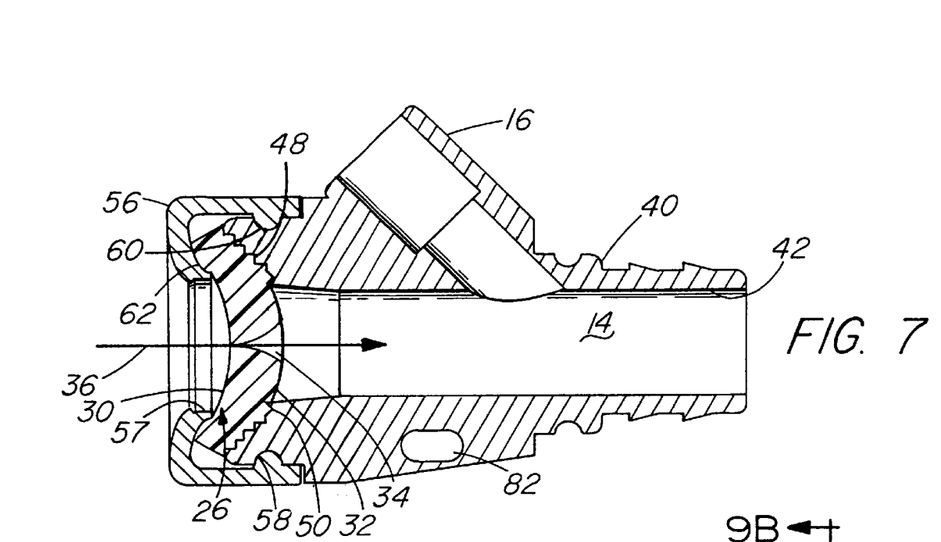
FIG. 7 is a cross-sectional view similar to that of FIG. 3, but with the seal shown in position between the cap and the body.

Concerning FIG. 7, the first 30 and second 32 faces of the seal 26 define a distal, downstream or insertion direction, the same direction as arrow 36, which is a preferred direction for movement either of a fluid through the at least one perforation 34 of the seal 26 (when the valve 10 is configured for use as a check valve), or of the catheter 20 or other interventional device during insertion into the introducer 12. The deflecting means 38 imparts a concave shape to the first face 30 of the seal 26 (FIG. 7), a shape which faces in a direction opposite to the preferred direction of movement (that is, opposite the arrow 36) through the at least one perforation 34. This opposite direction is therefore the upstream direction when the valve 10 is configured as a check valve, and the proximal direction when the valve 10 is incorporated in the catheter introducer 12.

Figure 4:
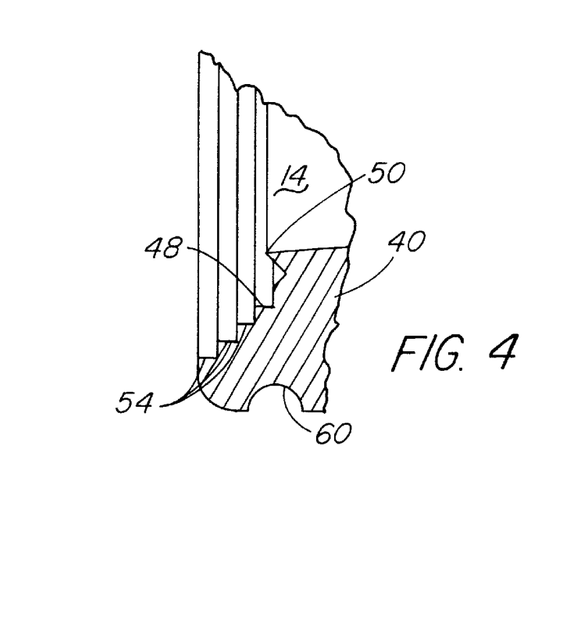
FIG. 4 is a detail of part of the view of FIG. 3.

This concave shape imparted to the first face 30 of the seal 26 embodies several of the advantages of the present invention. The deflecting means 38 therefore preferably comprises several further features for maintaining the concave shape of the first face 30 of the seal 26. For example, the cap 56 preferably includes an annular flange 62 extending towards the valve body 40. The annular flange 62 abuts the first face 30 of the seal 26, to impart a concave shape to the first face 30 of the seal 26. Similarly, the valve seat 48 also includes an annular flange 50 extending away from the valve body 40, abutting the second face 32 of the seal 26. The cooperation between annular flange 62 and annular flange 50 serves to impart a concave shape to the first face 30 of the seal 26, as well as to impart a convex shape to the second face 32 of the seal 26. To further ensure that the upstream, proximal, first face 30 of the seal 26 is concave in shape, the valve seat 48 is preferably formed as a series of annular steps 54 recessed in the valve body 40, the steps 54 being of decreasing radius in the preferred direction of movement through the at least one seal perforation 34 (FIG. 4). These ridged steps 54 serve to prevent the seal 26, when the periphery of the seal is pressed thereagainst by cap 56 thereby clamping the periphery, from being displaced during introduction, advancement or removal of the catheter 20 or another interventional device from the valve 10.

Figure 5A:
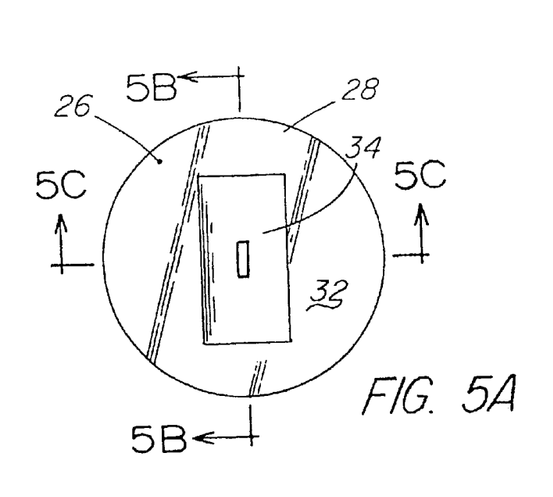
FIG. 5A is a rear, distal view of a seal employed in the preferred embodiment of the present invention.
Figure 5B:
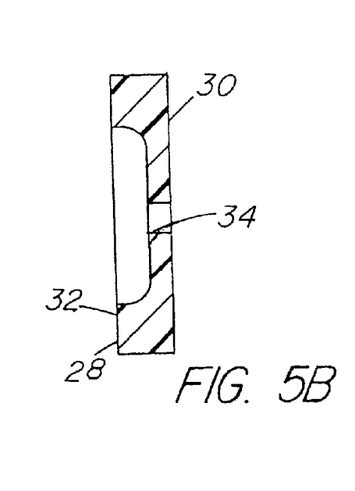
FIG. 5B is a cross-sectional view taken along line 5B—5B of FIG. 5A.
Figure 5C:
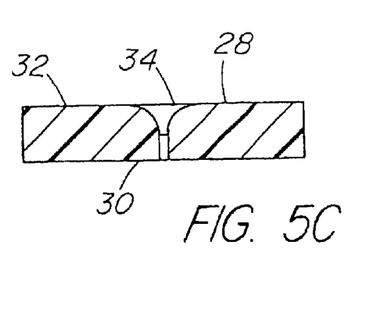
FIG. 5C is a cross-sectional view taken along line 5C—5C of FIG. 5A.
Figure 6A:
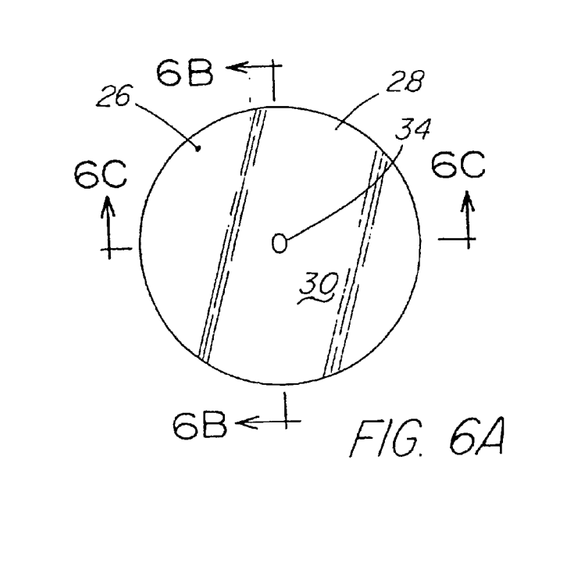
FIG. 6A is a front, proximal view of a seal employed in the preferred embodiment of the present invention.
Figure 6B:
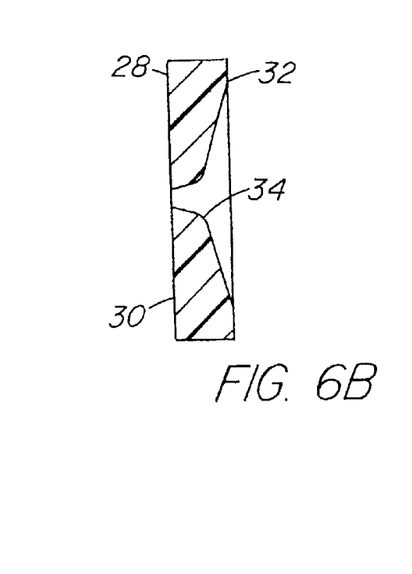
FIG. 6B is a cross-sectional view taken along line 6B—6B of FIG. 6A.
Figure 6C:
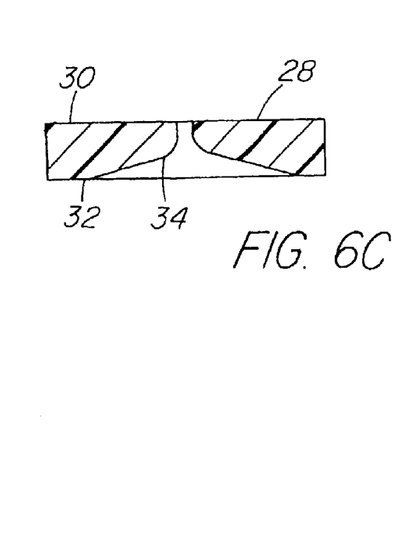
FIG. 6C is a cross-sectional view taken along line 6C—6C of FIG. 6A.

As more clearly shown in FIGS. 5A–5C (as well as in FIGS. 6A–6C), when the seal 26 is in its unstressed condition, that is, when not deflected by the cap 56 and the valve body 40, the at least one perforation 34 is wider at the second face 32 (the eventual downstream or distal face) than it is at the first face 30 (the eventual upstream or proximal face). This ensures that the at least one perforation will in fact close when the seal 26 is deflected by the deflecting means 38. Preferably, the at least one seal perforation 34 is Y-shaped when the seal 26 is in its unstressed condition. The "Y" is of course the cross-sectional shape of the at least one perforation 34 shown in FIG. 5C; as shown in FIG. 5B; however, the at least one perforation 34 has a significant width. Alternatively, as shown in FIGS. 6A–6C, the at least one perforation 34 can be oval in shape, possessing an increasing cross-section from the first seal face 30 to the second seal face 32.

Figure 12:
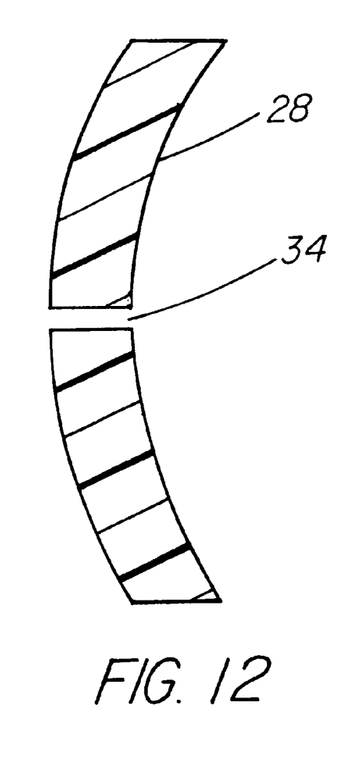
FIG. 12 depicts a cross-sectional view of another embodiment of the present invention and in particular a flexible seal with a perforation(s) extending therethrough when the seal is in a concave position.

FIG. 12 depicts a cross-sectional view of an alternative embodiment of the present invention in which flexible seal 28 is positioned in a concave position with open perforation 34 extending therethrough. The material of this alternative embodiment seal can be different from that previously described. It can be stiff yet resilient, but perforation 34 could have a soft lining. As a result, this alternative embodiment seal can be incorporated in a valve arrangement, similar to that of FIG. 3, in which there are two facing valve, seat 48 and eliminating flange 62. Cap 56 can be pushed into two positions; one position for the concave position or state of the seal and a second state representing the convex position of the seal depicted in FIG. 13.

Figure 13:
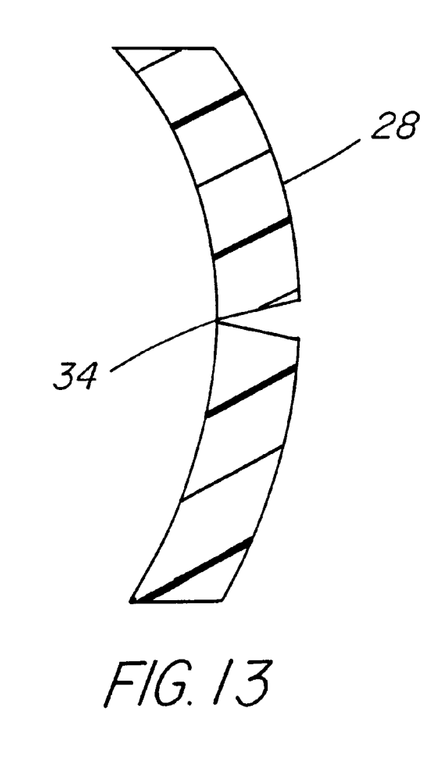
FIG. 13 depicts the seal of FIG. 12 when it is flexed into a convex position, thus closing the perforation extending therethrough.

FIG. 13 depicts seal 28 of FIG. 12 with the seal positioned in a second state or convex position as shown. In this second state or convex position, perforation 34 is closed thus preventing the flow of fluid therethrough. In this alternative embodiment seal, the seal is operated between at least two different positions or configurations, whereas the perforation 34 changes configuration between an open and a closed position as a result of varying the seal between its different positions or configurations.

Concerning FIGS. 1 & 3, use of the valve 10 of the present invention is remarkably straightforward. The introducer sheath 12 in which the valve 10 is contained is suitably positioned with respect to the patient. The guide wire 18, the catheter 20 or other interventional device is distally advanced in the direction of arrow 36 until it passes through a central opening 57 in the cap 56, then engages and passes through the at least one perforation 34 in the seal 26 (See FIG. 2). Returning to FIG. 7, the fact that the first face 30 of the seal 26 is concave in shape aids such engagement and passing. The concave shape, and the peripheral clamping, also prevents or substantially prevents inversion of the shape of the seal 26 when the guide wire 18, the catheter 20 or other interventional device is rotated or manipulated within the valve 10, or moved in a proximal direction opposite to the arrow 36.

The particularly disclosed arrangement of the cap 56 and valve body 40 has the advantage during use that it provides some space for the displacement of the material of the seal 26 when larger diameter catheters 20 or other devices are inserted; the seal 26 will expand during such insertion. Advantageously, a single size of seal 26 is useful for the entire range of sheath or catheter sizes from 9.5 Fr to 16 Fr. The disk 28 of the seal 26, by way of example, is preferably about 0.535 in. (13.6 mm) in diameter and 0.110 in. (2.8 mm) thick, with the at least one perforation sized in the proportions shown in the Figures. In such a case, hemostasis (sealing) is maintained not only for 0.020 in. (0.51 mm) diameter guide wires, but for diameters up to 16 Fr. catheters, balloons, dilators, stent introducers and other devices. A different sized valve is not required for each different French size, in contrast to several prior devices.

Figure 8:
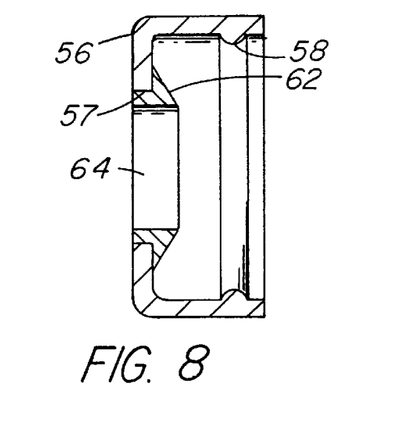
FIG. 8 is a cross-sectional view of a portion of another preferred embodiment of the present invention.

Alternate constructions for the cap 56, the valve body 40 or valve seat 48, and the seal 26 may facilitate manufacture or use of the valve 10. For example, as shown in FIG. 8, the flange 62 of the cap 56, which abuts the first face 30 of the seal 26, does not have to be formed integrally with the cap 56. Instead, the cap flange 62 can be formed as a separate ring 64 received in the cap 56, for example, press fit into the opening 57 of the cap 56. The apex of the cap flange 62 can conveniently lie at the inside diameter of the ring 64. The inside diameter of the cap flange 62 can be greater than or equal to the inside diameter of the annular flange 50, but as shown in FIG. 7 is preferably less than the inside diameter of the annular flange 50. Additional rings (not shown) can be added at the annular corners where the seal 26 meets the cap 56 and/or the valve body 40 or valve seat 48. Such rings would serve to further support or further shape the seal 26.

Figure 9A:
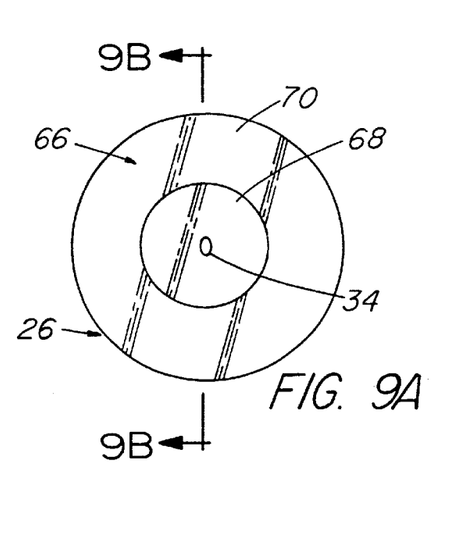
FIG. 9A is a front, proximal view of another seal employed in the preferred embodiment of the present invention.
Figure 9B:
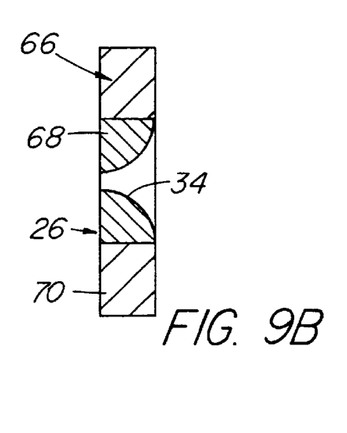
FIG. 9B is a cross-sectional view taken along line 9B—9B of FIG. 9A.
Figures 10, 11:
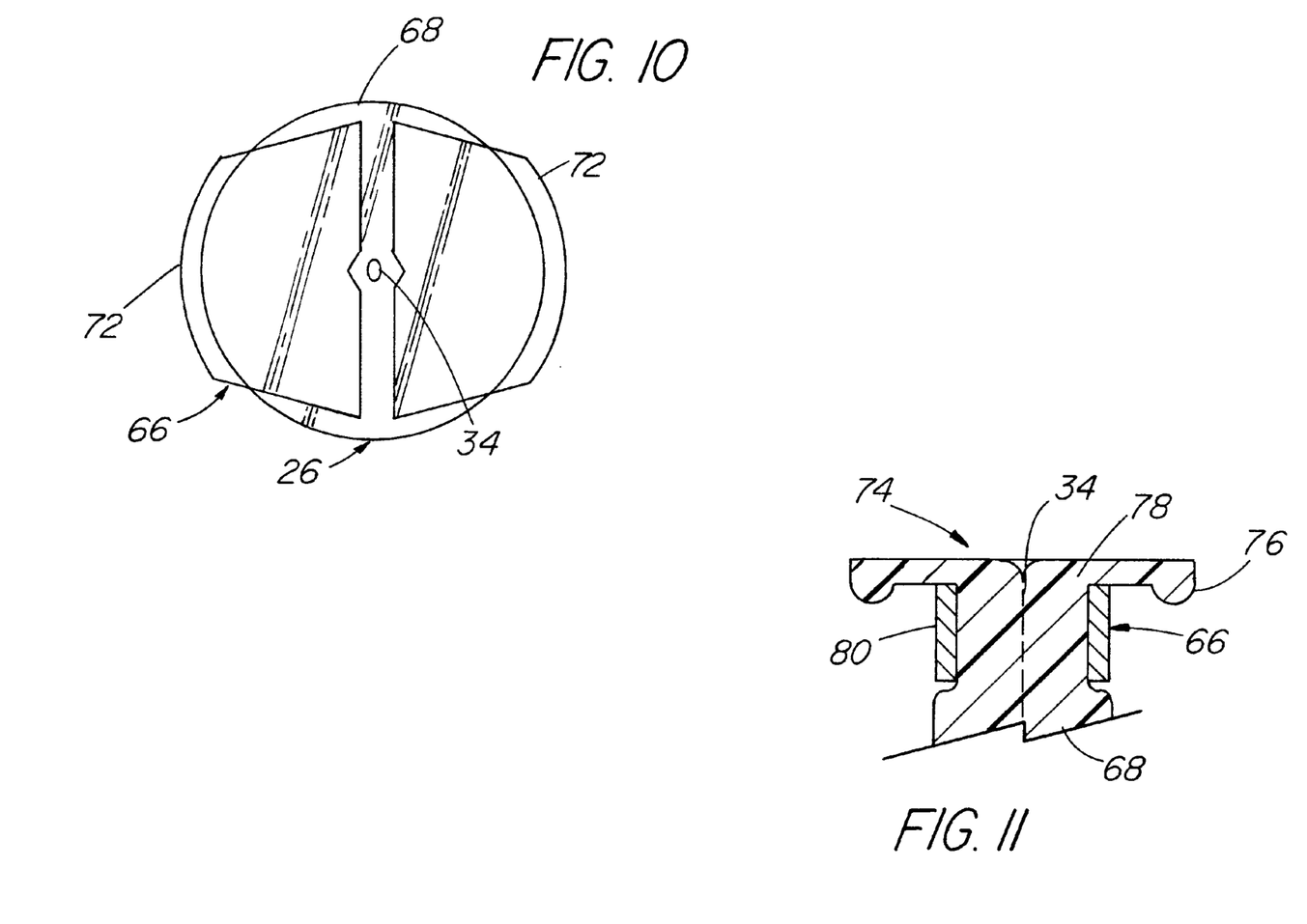
FIG. 10 is a front, proximal view of another seal employed in the preferred embodiment of the present invention.
FIG. 11 is a cross-sectional view of another seal employed in the preferred embodiment of the present invention.

As shown in FIGS. 9A–11, the deflecting means 38 can include a portion 66 carried by the low durometer seal 26 itself. For example, as shown in FIGS. 9A and 9B, the seal 26 can comprise a low durometer central portion 68 surrounded by an outer ring 70 composed of a material having a greater hardness. Indeed, the outer ring 70 conveniently can be, but need not necessarily be, composed of a thermoplastic elastomer. Alternatively, as shown in FIG. 10, the seal can comprise the low durometer central portion 68 and a pair of metal forms or wings 72 embedded in or affixed to a face of the central portion 68. The wings 72 can be composed of stainless steel, nitinol alloy, or another medical grade material more rigid than the low durometer central portion 68.

FIG. 11 shows a T-shaped seal 74 serving the same function as the seal 26, having a central body 78 with the at least one perforation 34 extending through it, and an annular outer, turned-over edge 76 spaced from but surrounding the central body 78. The body 78 and edge 76 are composed of the same elastomer as the seal 26. However, like the embodiments in FIGS. 9A–10, the seal 74 includes a portion 66 of the compressing means 38 on it. In particular, the portion 66 is an outer band or ring 80 surrounding the central body 78 but positioned radially inward of the outer edge 76 of the seal 74. The outer ring 80 can be composed of a thermoplastic elastomer having a hardness greater than that of the central body 78 (for example, a silicone band having a hardness of about 30 to 50 Shore A), or can be configured as a wire wrap or coil composed of stainless steel, nitinol alloy or another medical grade material. The ring 80 would be sufficiently strong to provide enough radial compression to close the at least one perforation 34 by itself. In use, the outer edge 76 of the seal 74 would be trapped against the valve body 40 by the cap 56, while the portion of the central body 78 below (distal to) the outer ring 80 could abut the fluid bore 42 of the valve body 40 directly. The valve seat 48 could then be omitted, or moved to a suitable location.

While disclosed as having particular utility as a hemostatic valve in an introducer sheath for a catheter or other interventional device, it should be apparent that the valve 10 of the present invention would also useful as an in-line check valve in the flow path of a medical fluid. The deflection of the seal 26, providing the proximal surface 30 of the seal 26 with a concave shape, would prevent the reversal of flow of a fluid through the perforation 34. This prevention of flow would exist even if fluid were present on the proximal side of the seal 26. The valve 10 could most easily be adapted to serve as an in-line check valve by simply replacing the cap 56 with a coupling or connector which is in turn connected to a supply of fluid. (The fluid bore 52 in the side arm 16, of course, should either be sealed or be connected to a suitable device or fluid coupling.) Other ways of adapting the valve 10 as a check valve in other structures should immediately be apparent to those skilled in this area, in light of the description of the valve provided above. Moreover, the valve 10 as disclosed could find good use in laparoscopic introducers, neuroendoscopic ports, or introducers for transthoracic surgical procedures, among a variety of others.

It is clear from the foregoing disclosure that the valve 10 of the present invention is particularly advantageous over prior check valves or introducer sheath seals in that it possesses a high degree of effectiveness when no catheter or other interventional device lies across the seal or valve, and provides an acceptable seal to catheters and other interventional devices having a wide range of diameters. The valve of the present invention also possesses a high resistance to tearing when penetrated by catheters or other interventional devices of large diameter. Use of a single seal eliminates the problem of trapped air or blood encountered in duckbill or combination disk/duckbill arrangements, and allows the valve of the present invention to hold vacuum or a negative pressure quite well. The valve of the present invention allows the easy passage of devices of a very wide range of diameters without interfering with tactile feedback from them. The valve of the present invention well tolerates repeated insertions and withdrawals of catheters or other interventional devices without any appreciable decrease in the performance characteristics of the seal or valve, especially with respect to leakage and "feel." Finally, the valve of the present invention is advantageous in that the deflection and the peripheral clamping placed upon the seal prevents undue inversion of the seal surface despite repeated removals and manipulations of devices lying across the valve.

The details of the construction or composition of the various elements of the valve 10 not otherwise disclosed are not believed to be critical to the achievement of the advantages of the present invention, so long as the elements possess the strength or flexibility needed for them to perform as disclosed. The selection of such details of construction are believed to be well within the ability of one of even rudimentary skills in this area, in view of the present disclosure.

What is claimed is:

1. A valve arrangement for controlling a flow of fluid therethrough, wherein the arrangement comprises a seal to be disposed in the fluid flow, the seal having at least one perforation to permit insertion of a medical device therethrough for fluid flow through the seal, where the perforation is open prior to medical device insertion and when the seal is unstressed prior to assembly of the valve, the seal further comprising a material, and the valve further includes a means for causing portions of the seal inwardly from a periphery thereof to be deflected in a direction farther into the valve in a manner sufficient to close the at least one perforation upon engagement of the means with the seal, whenever the seal is unpenetrated by the medical device.

2. The arrangement according to claim 1, wherein the seal is mounted so that it can be changed between one state and an other state, wherein when the seal is in the one state, the sidewalls of the at least one perforation are spaced apart, and when in the other state, the seal is deflected and the at least one perforation is closed to prevent fluid flow whenever the seal is unpenetrated by the medical device, and wherein the means serves to transfer the seal from the open state to the closed state.

3. The arrangement according to claim 2, wherein the material of the seal is sufficiently resilient to enable the seal to move between a concave state and a convex state, and wherein the at least one perforation is formed in such a manner that the at least one perforation is open in one of the states and closed in the other of the states.

4. The arrangement according to claim 3, wherein the means engages the first face of the seal and deflects the seal from a convex state to a concave state with respect to the first face.

5. The arrangement according to claim 1, wherein the material of the seal comprises low durometer thermoplastic.

6. The arrangement according to claim 5, wherein the material comprises a durometer of between 2 Shore A and 30 Shore A hardness.

7. The valve according to claim 5, wherein the material comprises a durometer of between 13 Shore A and 15 Shore A hardness.

8. The arrangement according to claim 1, wherein the material is compressible, and in that the means is designed to compress the material of the seal, at least in the region of the at least one perforation, in order to close the at least one perforation.

9. The arrangement according to claim 1, wherein when the seal is unstressed prior to valve assembly and insertion of a medical device therethrough, sidewalls of the perforation are spaced apart from the first face to the second face, and upon engagement of the seal by the means, the cross-sectional shape of the seal becomes deformed and the sidewalls of the perforation are also deformed to become closed at least at one location between the first face to the second face.

10. A valve for a fluid flow path, comprising:
a seal disposed in the fluid flow path, the seal being composed of a low durometer thermoplastic material having a hardness of no more than about 30 Shore A, and the seal having an undeflected condition in which the seal is shaped generally as a disk and the seal having a first and a second opposed face, the seal further having at least one perforation extending through the seal from the first face to the second face where the perforation is open prior to medical device insertion therethrough and when the seal is unstressed prior to assembly of the valve; and
means disposed about the fluid flow path for deflecting the seal so as to close the at least one perforation upon engagement of the means with the seal whenever the seal axially is unpenetrated by the medical device.

11. The valve according to claim 10, wherein the deflecting means comprises a valve body defining at least part of the fluid flow path.

12. The valve according to claim 11, wherein the deflecting means further comprises a valve seat formed in the valve body against which the seal is abutted.

13. The valve according to claim 12, wherein the deflecting means further comprises a cap engageable with the valve body, a periphery of the seal being compressed and clamped between the cap and the valve seat.

14. The valve according to claim 13, wherein the cap and the valve seat each include respective annular cap and valve seat flanges facing each other and abutting the first and second faces of the seal, respectively, with the annular valve seat flange having a diameter larger than that of the annular cap flange, whereby upon abutment with the seal the annular cap and valve seat flanges cooperate to impart a concave shape to the first face of the seal.

15. The valve according to claim 12, wherein the valve seat includes an annular flange extending toward the valve body and abutting the first face of the seal, imparting a concave shape to the first face of the seal.

16. The valve according to claim 12, wherein the first and second faces of the seal define a preferred direction of movement through the at least one perforation, and wherein the valve seat is formed as a series of steps in the valve body, the steps being of decreasing radii in the preferred direction of movement through the at least one perforation.

17. The valve according to claim 11, wherein the deflecting means further comprises a cap engageable with the valve body, a periphery of the seal being compressed and clamped between the cap and the valve body.

18. The valve according to claim 17, wherein the cap includes an annular flange extending towards the valve body and abutting the first face of the seal, imparting a concave shape to the first face of the seal.

19. The valve according to claim 8, wherein the annular cap flange comprises a ring received in the cap.

20. The valve according to claim 10, wherein the low durometer thermoplastic material has a resistance to tearing equivalent to that possessed by a thermoplastic styrene-ethylene/butylene-styrene block copolymer elastomer having a hardness of no more than about 30 Shore A.

21. The valve according to claim 20, wherein the material comprises a durometer of between 2 Shore A and 30 Shore A hardness.

22. The valve according to claim 20, wherein the material comprises a durometer of between 13 Shore A and 15 Shore A hardness.

23. The valve according to claim 10, wherein the first and second faces of the seal define a preferred direction of movement through the at least one perforation, and wherein the deflecting means imparts a concave shape to the first face of the seal facing opposite the preferred direction of movement through the at least one perforation.

24. The valve according to claim 10, wherein when the seal is in its undeflected condition and prior to insertion of a medical device through the perforation, the at least one perforation is open and is wider at the second face of the seal than at the first face of the seal.

25. The valve according to claim 10, wherein the at least one perforation is open and is Y-shaped when the seal is in its undeflected condition.

26. The valve according to claim 10, wherein the at least one perforation is open and is oval and possesses an increasing cross-section from the first face of the seal to the second face of the seal, when the seal is in its undeflected state.

27. The valve according to claim 10, wherein the seal comprises a thermoplastic styrene-ethylene/butylene-styrene block copolymer.

28. The valve according to claim 10, wherein a portion of the compressing means is affixed to the seal prior to valve assembly and is carried by the seal.

29. A self-sealing, penetrable, hemostatic valve for an introducer for an interventional device, the interventional device having a proximal end, and the valve including a generally disk-shaped seal receiving and sealing around the periphery of the interventional device when inserted in the introducer, the generally disk-shaped seal comprising a thermoplastic styrene-ethylene/butylene-styrene block copolymer having a hardness of no more than about 30 Shore A, and wherein the valve includes a body for deflecting the generally disk-shaped seal so as to present a concave face towards the proximal end of the interventional device.

30. The hemostatic valve according to claim 29, wherein the material comprises a durometer of between 2 Shore A and 30 Shore A hardness.

31. The hemostatic valve according to claim 29, wherein the material comprises a durometer of between 13 Shore A and 15 Shore A hardness.

32. The hemostatic valve according to claim 29, wherein the seal presents a nonconcave face towards the proximal end prior to compression during assembly of the valve.

33. The hemostatic valve according to claim 29, wherein the seal presents a convex face towards the proximal end prior to compression during assembly of the valve.

34. A valve having a fluid flow path therethrough, the valve comprising a perforated elastomeric disk closing the fluid flow path, wherein the disk further comprises a thermoplastic styrene-ethylene/butylene-styrene block copolymer having a hardness of no more than about 30 Shore A; and the perforated elastomeric disk having an undeflected condition with the perforated elastomeric disk further having an opposed first and a second faces and at least one perforation extending through the perforated elastomeric disk from the first face to the second face, the perforation having sidewalls that in the unstressed condition are spaced apart between the first face and the second face thereby being open prior to both assembly of the valve and insertion of a medical device therethrough; and means connected to the fluid flow path for deflecting the disk so as to close the at least one perforation in the perforated elastomeric disk axially upon deflection of the seal and prior to medical device insertion therethrough.

35. The valve according to claim 34, wherein the material comprises a durometer of between 2 Shore A and 30 Shore A hardness.

36. The valve according to claim 34, wherein the material comprises a durometer of between 13 Shore A and 15 Shore A hardness.

37. A valve defining a fluid flow path therethrough, comprising:

a seal to be disposed in the fluid flow path, the seal being composed of a very low durometer thermoplastic elastomeric styrene-ethylene/butylene-styrene block copolymer having a hardness of no more than about 30 Shore A, and the seal having an undeflected condition in which the seal is shaped generally as a disk and the seal further having an opposed first and a second faces and at least one perforation extending through the seal from the first face to the second face where the perforation is open prior to medical device insertion therethrough and when the seal is unstressed prior to assembly of the valve; and means connected to the fluid flow path for deflecting the seal so as to close the at least one perforation in the seal upon engagement of the means with the seal and prior to medical device insertion therethrough;

wherein the deflecting means comprises a valve body defining at least part of the flow path, a valve seat formed in the valve body and a cap engageable with the valve body, a periphery of the seal being compressed and clamped between the cap and the valve seat; and wherein the cap and the valve seat each include respective annular cap and valve seat flanges facing each other and abutting the first and second faces of the seal, respectively, imparting a concave shape to the first face of the seal;

wherein the first and second faces of the seal define a preferred direction of movement through the at least one perforation, and wherein the deflecting means imparts a concave shape to the first face of the facing opposite the preferred direction of movement through the at least one perforation; and wherein when the seal is in its unstressed condition, the at least one perforation is open and is wider at the second face of the seal than at the first face of the seal.

* * * * *